(12) United States Patent
Woods, Jr.

(10) Patent No.: US 7,029,704 B2
(45) Date of Patent: Apr. 18, 2006

(54) ANTI-ITCH SOLUTION

(76) Inventor: Clifford E. Woods, Jr., 507 Crump St., Raceland, KY (US) 41169

( * ) Notice: Subject to any disclaimer, the term of this patent is extended or adjusted under 35 U.S.C. 154(b) by 344 days.

(21) Appl. No.: 10/745,665

(22) Filed: Dec. 29, 2003

(65) Prior Publication Data

US 2005/0142213 A1 Jun. 30, 2005

(51) Int. Cl.
*A61K 31/19* (2006.01)
*A61K 33/00* (2006.01)
*A61K 33/40* (2006.01)
*A61K 36/73* (2006.01)
*A61P 17/00* (2006.01)
*A61P 17/04* (2006.01)
*A61P 31/10* (2006.01)

(52) U.S. Cl. ............. 424/616; 424/114; 424/717; 424/765; 514/557; 514/724; 514/858; 514/887

(58) Field of Classification Search ............. 424/114, 424/616, 717, 765; 514/557, 724, 858, 887
See application file for complete search history.

(56) References Cited

U.S. PATENT DOCUMENTS

| | | |
|---|---|---|
| 3,704,227 A | 11/1972 | Hill |
| 4,485,091 A | 11/1984 | Fitton |
| 4,557,898 A | 12/1985 | Greene et al. |
| 4,812,308 A | 3/1989 | Winston et al. |
| 4,925,655 A | 5/1990 | Smigel et al. |
| 5,403,578 A | 4/1995 | Gordon |
| 5,411,750 A | 5/1995 | Lajoie et al. |
| 5,518,727 A | 5/1996 | Lajoie et al. |
| 5,523,012 A | 6/1996 | Winterton et al. |
| 5,645,840 A | 7/1997 | Lajoie et al. |
| 5,736,582 A | 4/1998 | Devillez |
| 5,965,110 A | 10/1999 | Arnold |
| 5,993,853 A * | 11/1999 | Manning et al. ............ 424/456 |
| 6,063,364 A * | 5/2000 | Makos ........................ 424/49 |
| 2003/0147941 A1 | 8/2003 | Koenig et al. |
| 2003/0157195 A1 | 8/2003 | Bartels |

FOREIGN PATENT DOCUMENTS

| | | |
|---|---|---|
| EP | 0 279 130 A2 | 8/1988 |
| WO | WO 98/18439 | 5/1998 |

OTHER PUBLICATIONS

Tinea Infections: Athlete's Foot, Jock Itch and Ringworm. American Academy of Family Physicians, Nov. 2005 [retrieved on Jan. 31, 2006]. Retrieved from the Internet: <URL: http://familydoctor.org/316.xml>.*

Athlete's Foot. American Podiatric Medical Association, Inc. 2006 [retrieved on Jan. 31, 2006]. Retrieved from the Internet: <URL: www.apma.org/s_apma/doc.asp?cid=317&did=9386>.*

HCAPLUS Abstract, accession No. 1997:726818 (1997), Retrieved from STN Online, Chemical Abstracts Service (Columbus, Ohio).*

HCAPLUS Abstract, accession No. 1966:97148 (1966), Retrieved from STN Online, Chemical Abstracts Service (Columbus, Ohio).*

* cited by examiner

*Primary Examiner*—John Pak
(74) *Attorney, Agent, or Firm*—Richard C. Litman

(57) ABSTRACT

The anti-itch solution is a solution of hydrogen peroxide, sodium bicarbonate and apple cider vinegar applied to feet to prevent a common fungal infection of feet known as "athlete's foot".

6 Claims, No Drawings

ANTI-ITCH SOLUTION

BACKGROUND OF THE INVENTION

1. Field of the Invention

The present invention relates generally to foot powder. More specifically, the invention is an anti-itch powder for preventing an infection of athlete's foot.

2. Description of the Related Art

The related art of interest describes various medications for treating the common athlete's feet infection, but none discloses the present invention. There is a need for an economical fungicide medicament for curing an infection of athlete's foot.

U.S. Pat. No. 4,812,308 issued on Mar. 14, 1989, to Anthony Winston et al. describes a hydrogen peroxide-releasing tooth powder composition comprising sodium bicarbonate, sodium percarbonate in combination with flavoring agents, sweeteners, fluoridating agents, abrasives, and/or additional adjuvants. The composition is distinguishable for requiring sodium percarbonate, flavoring agents, sweeteners, fluoridating agents, and abrasives, and its use as a dentifrice.

Patent Cooperation Treaty Application No. WO 98/183439 published on May 7, 1998, for Liezl G. Peterson et al. describes a body deodorant powder composition comprising a perfume-free powder, odor absorbing agents such as 0.1% to 25 wt. % of uncomplexed cyclodextrin, and a powder carrier. 5% to 60% by weight of a moisture absorbing composition. Additional odor controlling agents selected from the group consisting of zeolites, activated charcoal, sodium bicarbonate, antimicrobial agents, and antiperspirants. The composition is distinguishable for requiring perfume-free powder, odor absorbing cyclodextrin, and a powder carrier, U.S. Pat. No. 4,925,655 issued on May 15, 1990, to Irwin Smigel et al. describes a powder composition for forming a mouthwash solution comprising calcium peroxide and sodium perborate in equal amounts of calcium peroxide, and sodium bicarbonate in the largest amount. However, sodium sacchrinate potassium carbonate and hydrated silicate are necessary in significant amounts. The composition is distinguishable for being in powder form and requiring numerous amounts of at least ten more significant ingredients.

U.S. Patent Application Publication No. U.S. 2003/0147941 A1 published on Aug. 7, 2003, for David W. Koenig et al. describes training pants and diapers containing products for controlling microbial organic compound production comprising a 0.01 to 5% by wt. carbohydrate-hydrogen peroxide in a crystalline powder composition which produces an oxygen stream when wetted. The composition is distinguishable for requiring a major proportion of baby powder.

U.S. Patent Application Publication No. U.S. 2003/0157195 A1 published on Aug. 21, 2003, for Jennifer F. Bartels describes a topical cream, dusting powder, spray, bath soak, and effervescent tablet composition for treating diaper rashes and skin irritations caused by acidic secretions comprising a) a pH-raising ingredient selected from the group consisting of sodium bicarbonate, magnesium hydroxide, calcium carbonate, aluminum hydroxide, and mixtures thereof; b) an anhydrous base ointment; c) polysorbate 80; d) purified water, and e) butylated hydroxy toluene. The pH is adjusted to 7.0 to 10.4 by acetic acid. The composition is distinguishable for requiring magnesium hydroxide, calcium carbonate, aluminum hydroxide, and mixtures thereof.

U.S. Pat. No. 3,704,227 issued on Nov. 28, 1972, to William H. Hill describing denture cleanser compositions comprising sodium carbonate monohydrate combined with sodium perborate, dipotassium persulfate, and trisodium phosphate. The compositions are distinguishable for requiring major amounts of sodium perborate, dipotassium persulfate, and trisodium phosphate.

U.S. Pat. No. 4,485,091 issued on Nov. 27, 1984, to Harry Fitton describes a dermatological composition in the form of a cream, lotion or gel containing hydrogen peroxide in a buffered acidic aqueous medium, but not containing sodium bicarbonate. The composition is distinguishable for requiring hydrogen peroxide without sodium bicarbonate.

U.S. Pat. No. 5,403,578 issued on Apr. 4, 1995, to Norman Gordon describes a stable tooth and gum dentifrice paste with microencapsulation comprising a carrier containing sorbitol, glycerine urea, and hydrated silica with added fluoride, sodium bicarbonate, pyrophosphate, and calcium peroxide. The composition is distinguishable for requiring enumerable ingredients besides sodium bicarbonate and calcium peroxide.

U.S. Pat. No. 5,411,750 issued on May 2, 1995, U.S. Pat. No. 5,518,727, issued on May 21, 1996, and U.S. Pat. No. 5,645,840, issued on Jul. 8, 1997, to M. Stephen Lajoie et al. describe an alkali metal bicarbonate powder exhibiting antibacterial and antifungal activity. The products are distinguishable for lacking hydrogen peroxide.

U.S. Pat. No. 5,523,012 issued on Jun. 4, 1996, to Lynn C. Winterton et al. describes buffered hydrogen peroxide solutions for disinfecting formulations for contact lenses are improved by incorporating a surface active agent. The compositions are distinguishable for lacking sodium bicarbonate.

U.S. Pat. No. 5,736,582 issued on Apr. 7, 1998, to Richard L. Devillez describes a medicating human skin disorders using hydrogen peroxide, but not with sodium bicarbonate. Salicylic acid and dimethyl isosorbide in aqueous solution are other ingredients.

U.S. Pat. No. 5,965,110, issued on Oct. 12, 1999, to Michael J. Arnold describes a plaque adsorbent oral or effervescent dentifrice composition in kit form comprising a debriding product, a hydrogen peroxide product, and a bicarbonate dentifrice. The composition is distinguishable for being required for dental use.

European Patent Application Publication No. 0 279 130 A2 published on Aug. 24, 1988, for Anthony Winston et al. describes a hydrogen peroxide-releasing tooth powder comprising a sodium bicarbonate and safe hydrogen peroxide in combination with flavoring agents, sweeteners, fluoridating agents, abrasives, surfactants and/or additional adjuvants. The composition is distinguishable for limited to dental use and requiring flavoring agents, sweeteners, fluoridating agents, abrasive, surfactants and/or additional adjuvants.

None of the above inventions and patents, taken either singly or in combination, is seen to describe the instant invention as claimed. Thus, an anti-itch solution solving the aforementioned problems is desired.

SUMMARY OF THE INVENTION

The invention is a foot medication composition for curing and preventing an athlete's feet infection. Sodium bicarbonate, a hydrogen peroxide solution and apple cider vinegar are mixed in the proportions of one and a half level teaspoons of sodium bicarbonate, 2.5 to 3 fluid ounces of aqueous hydrogen peroxide, and 0.5 to 2 fluid ounces of apple cider vinegar. The medication is applied to one's feet daily and preferably after bathing.

Accordingly, it is a principal object of the invention to provide an anti-itch foot medication composition.

It is another object of the invention to provide a foot powder medication composition containing sodium bicarbonate.

It is a further object of the invention to provide a foot powder medication composition containing sodium bicarbonate and hydrogen peroxide solution.

Still another object of the invention is to provide a foot powder medication composition consisting of sodium bicarbonate, hydrogen peroxide solution, and apple cider vinegar.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENT

The present invention is directed to an anti-itch solution for treating and preventing fungus growth on one's feet such as athlete's foot. People who exercise frequently in aquatic centers, spas, exercise centers, and the like have to prevent getting athlete's foot infection, because it is inevitable that others with infected feet patronize the same facilities. Thus, a preventative composition is illustrated to afford such protection, since one must exercise and frequent such facilities.

A four fluid ounce composition comprises: 2.5 to 3.0 fluid ounces of conventional hydrogen peroxide solution (2.75 fluid ounces preferred); 1 to 2 level teaspoons (1.5 level teaspoons preferred) of conventional baking soda; and 0.5 to 1 fluid ounce (0.75 fluid ounce preferred) of apple cider vinegar. The ingredients are mixed in the order listed, but the addition of the third ingredient must be done with some precaution to avoid excessive bubbling if mixed too quickly. After mixing the ingredients, there is no problem with effervescence.

Thus, it has been determined that use of this anti-itch composition is effective in preventing the infection of athlete's foot.

It is to be understood that the present invention is not limited to the embodiment described above, but encompasses any and all embodiments within the scope of the following claims.

I claim:

1. An anti-itch solution for protection against athlete's foot infection comprising effective amounts of hydrogen peroxide, baking soda, and apple cider vinegar, wherein the ratio of baking soda to apple cider vinegar is 1.0 to 2.0 level teaspoons of baking soda per 0.5 to 1 fluid ounce of apple cider vinegar.

2. The anti-itch solution according to claim 1, wherein the hydrogen peroxide solution is present in the range of 2.5 to 3 fluid ounces.

3. The anti-itch solution according to claim 1, wherein the hydrogen peroxide solution is present in the amount of 2.75 fluid ounces.

4. The anti-itch solution according to claim 1, wherein the baking soda is present in the amount of 1.5 level teaspoons.

5. The anti-itch solution according to claim 1, wherein the apple cider vinegar is present in the amount of 0.75 fluid ounce.

6. An anti-itch solution for protection against athlete's foot infection comprising:
   2.5 to 3 fluid ounces of hydrogen peroxide solution;
   1.5 level teaspoons of baking soda; and
   0.5 to 1 fluid ounce of apple cider vinegar.

\* \* \* \* \*